US 6,632,271 B2
United States Patent
Robertson et al.
Date of Patent: *Oct. 14, 2003

(54) MBI BIOAEROSOL VORTEX CASSETTE

(76) Inventors: Larry Don Robertson, 2484 FM 39 North, Jewett, TX (US) 75846; Robert Allen Garrison, 1635 Mockingbird La., Southlake, TX (US) 76092

( * ) Notice: Subject to any disclaimer, the term of this patent is extended or adjusted under 35 U.S.C. 154(b) by 0 days.

This patent is subject to a terminal disclaimer.

(21) Appl. No.: 09/906,424

(22) Filed: Jul. 17, 2001

(65) Prior Publication Data

US 2003/0015098 A1 Jan. 23, 2003

Related U.S. Application Data

(63) Continuation-in-part of application No. 09/641,503, filed on Aug. 21, 2000, now Pat. No. 6,517,593.

(51) Int. Cl.$^7$ .............................. B01D 46/00; G01N 1/00
(52) U.S. Cl. ..................... 96/413; 55/337; 73/863.23
(58) Field of Search ............................. 96/413; 55/337; 73/28.01, 863.21, 863.23; 435/5, 30, 34

(56) References Cited

U.S. PATENT DOCUMENTS

| 3,564,843 A | * | 2/1971 | Hirschler, Jr. et al. ........ 55/337 |
| 3,980,563 A | | 9/1976 | Greutert et al. |
| 4,249,655 A | * | 2/1981 | Patureau et al. ............ 209/237 |
| 4,606,232 A | * | 8/1986 | Prodl ........................ 73/863.23 |
| 4,796,475 A | * | 1/1989 | Marple ...................... 422/101 |
| 4,939,096 A | | 7/1990 | Tonelli |
| 5,081,017 A | * | 1/1992 | Longoria ................... 210/455 |
| 5,254,147 A | * | 10/1993 | Finke .......................... 15/353 |
| 5,701,012 A | * | 12/1997 | Ho ......................... 250/461.2 |
| 5,874,237 A | * | 2/1999 | Hull et al. ............... 435/283.1 |
| 5,898,114 A | * | 4/1999 | Basch et al. ............. 73/863.23 |
| 5,942,699 A | * | 8/1999 | Ornath et al. ............ 73/863.12 |
| 6,101,886 A | * | 8/2000 | Brenizer et al. ............. 55/308 |
| 6,103,534 A | | 8/2000 | Stenger et al. |
| 6,517,593 B1 | * | 2/2003 | Robertson et al. ......... 55/385.1 |
| 2003/0075048 A1 | * | 4/2003 | Jordan, Sr. et al. .......... 95/285 |

FOREIGN PATENT DOCUMENTS

JP          7-294393 A     * 11/1995

* cited by examiner

*Primary Examiner*—Duane Smith
*Assistant Examiner*—Frank M. Lawrence
(74) *Attorney, Agent, or Firm*—Lowe Hauptman Gilman & Berner, LLP

(57) ABSTRACT

An insert for a cassette that is adapted to sample particulate matter in air. The insert has an upstream end that is circular and a downstream end that is flange shaped with substantially smooth walls between the upstream and downstream ends of the insert. The cassette with the insert disposed therein is also described.

17 Claims, 4 Drawing Sheets

MBI BIOAEROSOL VORTEX CASSETTE

This application is a continuation in part of application Ser. No. 09/641,503, filed Aug. 21, 2000, now U.S. Pat. No. 6,517,593, the entire contents of which are incorporated herein by reference.

The 25-millimeter (mm) cassette equipment with a 0.8-micron mixed cellulose ester (MCE) filters are routinely used in the practice of industrial hygiene. More specifically, these cassettes are commonly used in the evaluation of airborne concentrations of asbestos. Bioaerosol agents can be recovered with the standard use of these cassettes, however; problems exist with regard to analyses of data collected by standard methodologies. The MBI Bioaerosol Vortex Cassette is designed specifically for the collection and identification of airborne biological agents such as fungal spores and pollen. Typically most fungal bioaerosol components are above 1 micron in size. Hence, filters having a pore size just below 1 micron are useful in the filtration of fungal bioparticulate from the air without excessive air resistance. After collection, filters can be prepared for culture and/or viewed microscopically. Filtration technologies vastly improve recovery efficiency. In the past, direct filter examination has proven impractical because of the time required to collect samples, desiccation of recovered spores, as well as, increased man-hour and equipment costs. However, the MBI Bioaerosol Vortex Cassette represents a new design that concentrates fungal bioparticulate into a distinct zone on the receiving filter. The concentration of recovered agents in effect reduces the collection area of the MCE filter thus allowing a reduction in sampling time without compromising detection levels or filter integrity. The MBI Bioaerosol Vortex Cassette capitalizes on standard and accepted sampling methodologies, but now expands the use of 0.8 micron MCE filtration collection methodology into the field of fungal and other bioaerosol identification and reporting.

BACKGROUND OF THE INVENTION

Air sampling is used to quantify and qualify the contents of an environment. Laboratory analyses of the samples provide critical information relative to the potential exposure to harmful agents. Bioaerosol sampling focuses these processes on particles of biological origin. These agents include, but are not limited to, viable and non-viable fungal spores, bacteria, pollen, skin cells, fibers and insect parts.

The 25-millimeter (mm) cassette equipment with a 0.8-micron mixed cellulose ester (MCE) filters are routinely used in the practice of industrial hygiene. More specifically, these cassettes are commonly used in the evaluation of airborne concentrations of asbestos. Bioaerosol agents can be recovered with the standard use of these cassettes, however; problems exist with regard to analyses of data collected by standard methodologies. Bioaerosol components are usually in far less airborne concentrations when compared to asbestos related industrial hygiene and/or abatement projects. Therefore, it becomes necessary to sample greater volumes of air in order to achieve appropriate detectable levels of bioaerosols using MCE filter technology. Airflow turbulence occur if 0.8-micron mixed cellulose ester filters are exposed to air velocities over 15 liters per minute (L/m) that result in non-uniform particle distribution.

Therefore, the rate of airflow cannot be adjusted over 15 L/m without potential damage to the MCE filter. Therefore, sample time is the only parameter available for manipulation. Under normal conditions, several hours of sampling are required in order to obtained an appropriate volume of air for bioaerosol analyses. These time constraints are problematic, especially when considering the costs related to on-site technical man-hours and/or the need for additional equipment for each individual sample location. The MBI Bioaerosol Vortex Cassette has the unique ability to reduce sampling time to minutes without damaging MCE filters and thereby creating a highly efficient and effective bioaerosols recovery unit.

BRIEF SUMMARY OF INVENTION

The MBI Bioaerosol Vortex Cassette is designed for a specific niche in the marketplace. Until recently, bioaerosol sampling has been performed using two basic types of collection methologies; filtration and impact. Filtration methodologies utilize filter cassettes that are equipped with filters having a variety of design, such as rectangular or oval or circular, components, and pore sizes. Typically, most fungal bioaerosol material components are above 1 micron in size. Hence, filters having a pore size just below 1 micron are useful in the filtration of fungal bioparticulate from the air without excessive air resistance. After collection, filters can be prepared for culture and/or viewed microscopically. The se of filters for fungal culture has proven to be inefficient with regard to recovery and is typically not recommends. Direct observation under a microscope is possible, however; typically the sampling time required to collect detectable amounts rendered this sampling technique as implausible. Impacting methods have emerged as the principal means to evaluate airborne fungal bioparticulate. Impacting occurs directly into agar-media surfaces for culture or on to special fixatives for direct microscopic examination. While some benefits exist with respect to culture recovery, the overall process inherently introduces a bias of recovery and generally requires at least 5–7 days for incubation prior to analysis. Impacting directly on to specific fixatives does allow the potential for immediate analysis, however, some limits exist with regard to identification and classification.

Regardless, impaction methods remain vulnerable to a variety of parameters that effect "recovery efficiency". These factors include airflow, particle size, aerodynamics, etc. . . . No impacting sampler is 100% efficient. Therefore, some percentage bioparticulate merely passes through the sampler and remains undetected.

Filtration technologies vastly improve recovery efficiency. The selection of filter pore sizes that are below the dimensions of fungal particulate ensures retention. Culture from filters have demonstrate relatively low recovery and are not generally recommended for air sampling, however; direct microscopic examination of filters offers an improved recovery efficiency over traditional impacting methods. In the past, direct filter examination has proven impractical because of the time required to collect samples, desiccation of recovered spores, as well as, increased man-hour and equipment costs. However, the MBI Bioaerosol Vortex Cassette represents a new design that concentrates fungal bioparticulate into a distinct zone on the receiving filter. The concentration of recovered agents in effect reduces the collection area of the MCE filter thus allowing a reduction in sampling time without compromising detection levels or filter integrity. The MBI Bioaerosol Vortex Cassette capitalizes on standard and accepted sampling methodologies, but now expands the use of 0.8 micron MCE filtration collection methodology into the field of fungal and other bioaerosol identification and reporting.

DETAILED DESCRIPTION OF THE DRAWINGS

Figure 1:
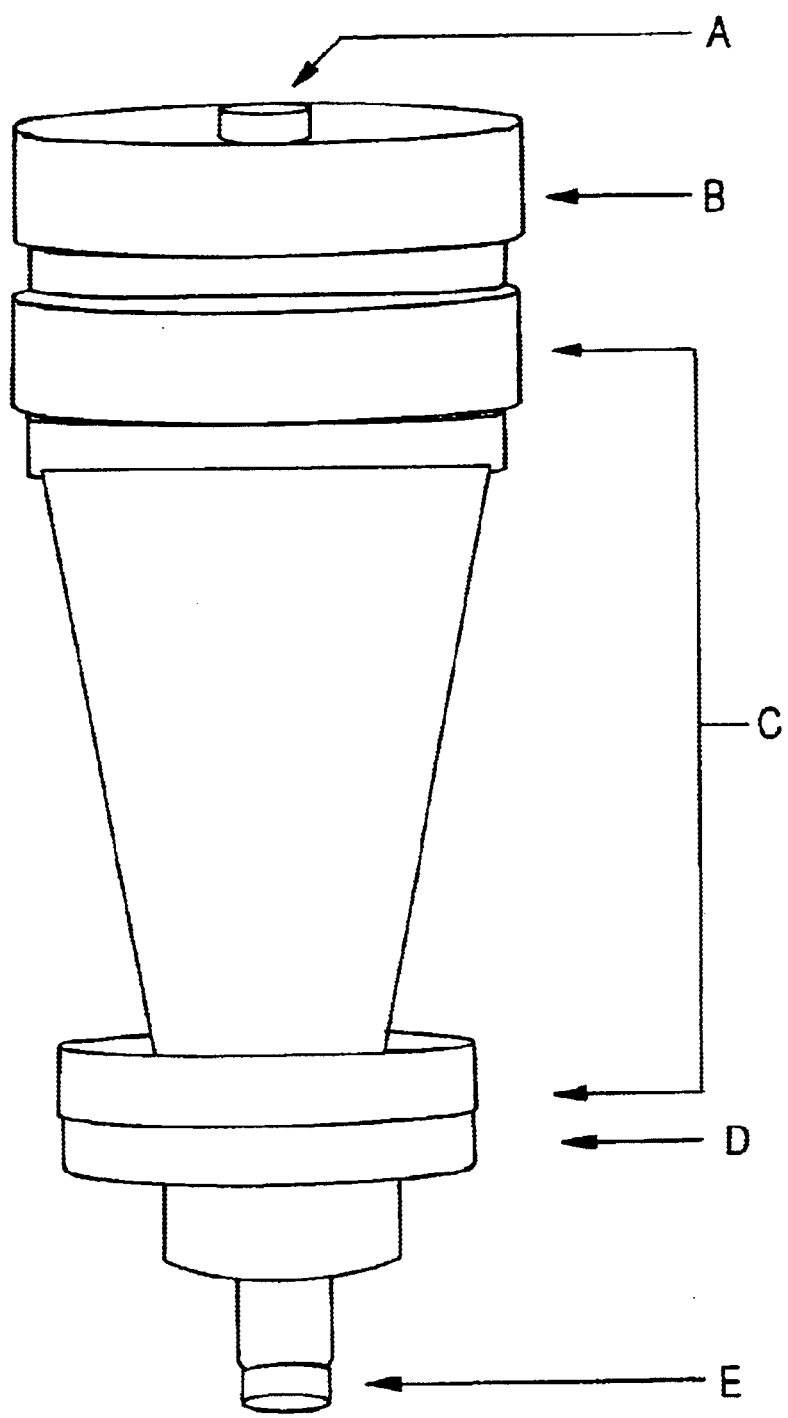
FIG. 1 depicts a standard 25-millimeter (mm) cassette containing the MBI Bioaerosol Vortex Cassette.

FIG. 1 depicts a standard 25-millimeter (mm) cassette containing the MBI Bioaerosol Vortex Cassette. The barrel (C) is wholly adaptable to existing designs and technologies utilizing 25-mm cassettes. Reference A identifies the in-port tubing cap. The tubing cap can be removed to allow the linking with tubing for remote collections in generally inaccessible spaces such as interstitial walls, crawl spaces, attics, etc. . . . Reference B identifies the intake cap. The intake cap (B) is removed prior to the collection air and/or surface samples. The MBI Bioaerosol Vortex Cassette barrel (C) is attached to the filter canister (D). The filter canister contains a retention layer (G) supporting a 0.8-micron MCE filter (F) (not visible in this illustration). Reference E identifies the out-port tubing cap. The out-port tubing cap is removed to allow the attachment of a suction tube from a vacuum pump having a flow rate capacity between one (1) and fifteen (15) liters per minute. Operation of the vacuum pump draws air into the cassette. The MBI Bioaerosol Vortex Cassette collects, funnels, concentrates, and deposit particulate onto the 0.8 micron MCE filter contained in the filter canister.

Figure 2:
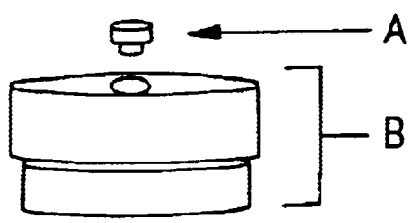
FIG. 2 is an exploded front and side view of the 25-millimeter (mm) cassette containing the MBI Bioaerosol Vortex Cassette.
Figure 2:
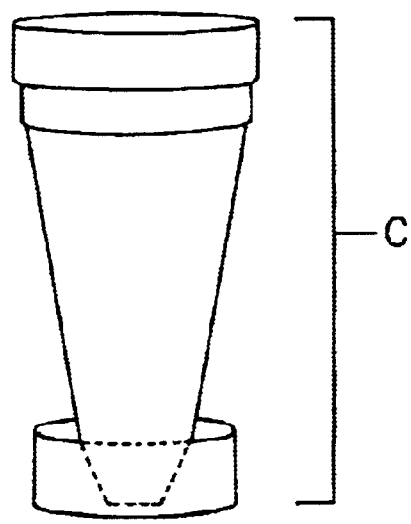
Figure 2:
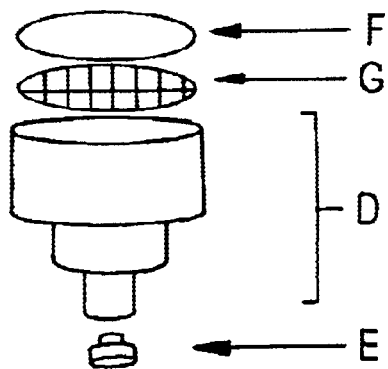

FIG. 2 is an exploded front and side view of the 25-millimeter (mm) cassette containing the MBI Bioaerosol Vortex Cassette. The insert is wholly adaptable to existing designs and technologies utilizing 25-mm cassettes. Reference A identifies the in-port tubing cap. The tubing cap can be removed to allow the linking with tubing for remote collections in generally inaccessible spaces such as interstitial walls, crawl spaces, attics, etc. . . . Reference B identifies the intake cap. The intake cap (B) is removed prior to the collection air and/or surface samples. The MBI Bioaerosol Vortex Cassette barrel (C) is attached to the filter canister (D). The filter canister contains a retention layer (G) supporting a 0.8-micron MCE filter (F). Reference E identifies the out-port tubing cap. The out-port tubing cap is removed to allow the attachment of a suction tube from a vacuum pump having a flow rate capacity between one (1) and fifteen (15) liters per minute. Operation of the vacuum pump draws air into the cassette. The MBI Bioaerosol Vortex Cassette collects, funnels, concentrates, and deposit particulate onto the 0.8 micron MCE filter contained in the filter canister.

Figure 3:
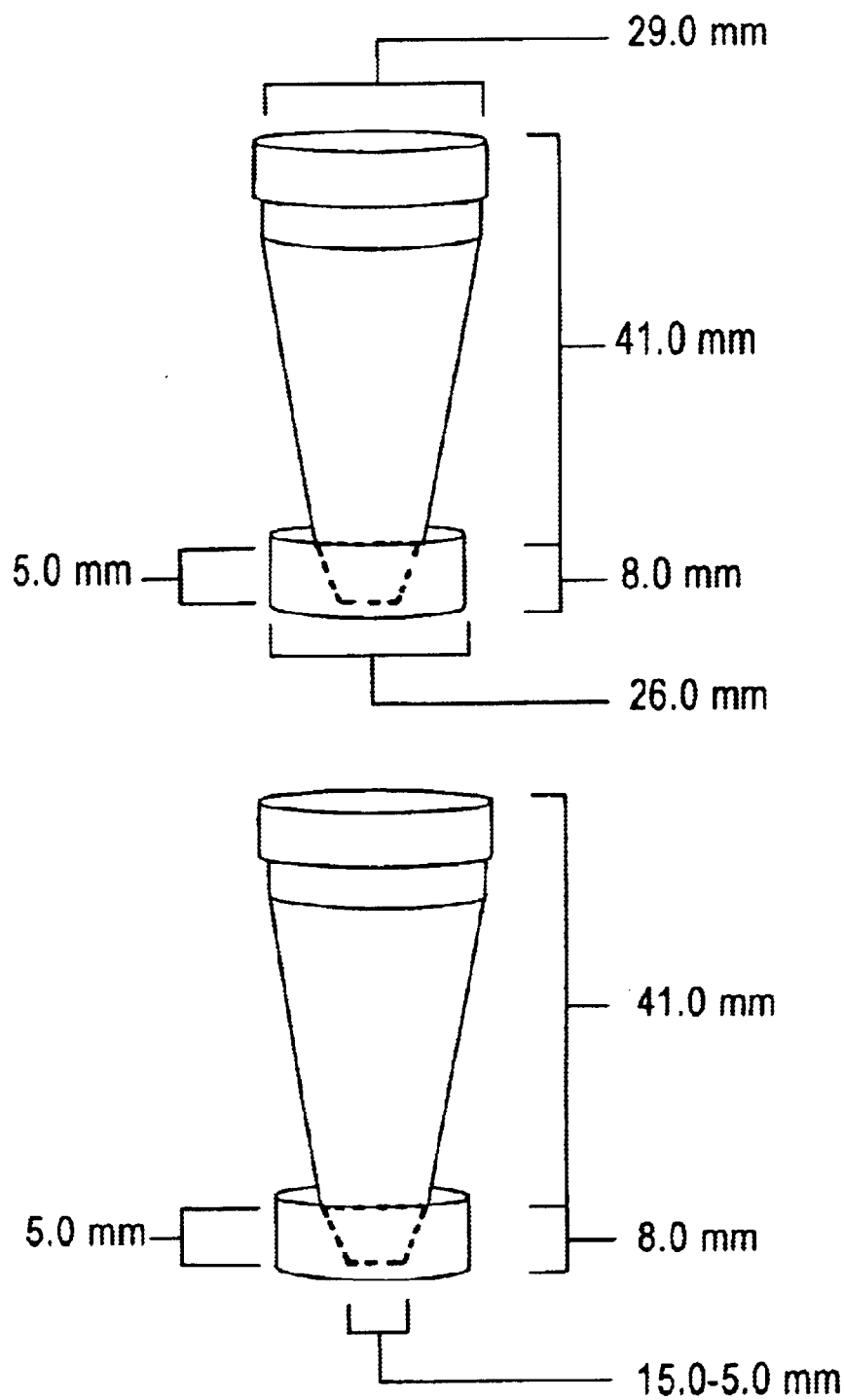
FIG. 3 are side front and side views of the MBI Bioaerosol Vortex Cassette with general dimensions.
Figure 4:
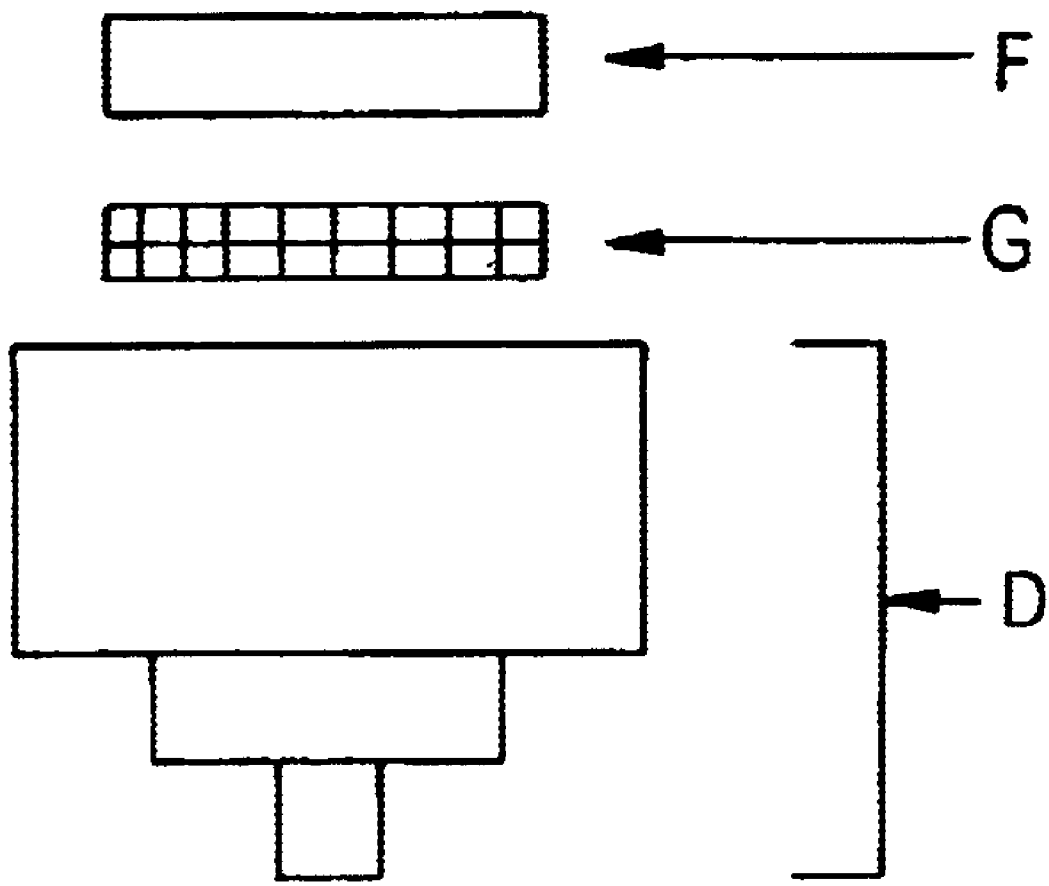
FIG. 4 is an exploded side view, similar to FIG. 2, of an additional aspect of this invention.

FIG. 3 are front and side views of the MBI Bioaerosol Vortex Cassette with general dimensions. The opening of the MBI Bioaerosol Vortex Cassette barrel has an upper diameter of 29.0 millimeters (mm). The upper 16-mm has two distinct beveled layers capable of attaching to standard a 25 mm intake cap. The upper layer is approximately 7.5 mm in length. Total length of the barrel is approximately 50.0 mm. The internal barrel has a design length of approximately 46.0 mm which will terminate approximately 1–2 mm from the surface of the 0.8-micron MCE filter contained in the filter canister. However, the mechanism will be design such that the insert can actual touch the surface of the filter to enhance collection recovery under certain conditions. The insert begins as a circular structure that transitions into a vortex that narrows from top to bottom. The illustration indicates the bottom opening has outer diameter of between 5 and 15.0 mm and generally designed to create a filter deposition trace having a diameter of 5 and 15 mm. However, these dimensions will vary in production, thus allowing the insert to specifically target particles of specific mass and aerodynamic character.

What is claimed is:

1. An insert, adapted to be disposed in a cassette, wherein said cassette is adapted to trap solid particles from an ambient environment comprising gas containing a quantity of gas born solid particles, or solid particles on a surface, wherein said insert comprises a combination of:

a structure surrounding an internal conduit having a larger cross section upstream end adapted to communicate with said a gas containing said solid particles, a downstream end that has a substantially smaller cross section than said upstream end, and at least one wall defining said internal conduit disposed between said ends;

wherein the shape of said internal conduit, having a reduction in cross section from said upstream end to said downstream end, is adapted to cause the concentration of said solid particles in said gas at said downstream end of said conduit to become more concentrated in said gas than the concentration of said solid particles in said gas at said upstream end of said conduit; and a filter so structured and operatively associated with said downstream end of said conduit that all gas in said conduit passes through said filter, wherein said filter and said conduit structures cooperate to cause gas borne solid particles of a predetermined size that pass through said conduit to become entrapped by at least a portion of said filter;

wherein said insert is adapted to communicate with vacuum generating apparatus disposed downstream of said filter that is adapted to cause ambient gas to be sucked through said upstream end of said conduit, said conduit, said downstream end of said conduit and said filter, and to be exhausted back to ambient downstream of said filter.

2. The insert as claimed in claim 1 wherein said filter medium is spaced downstream from said downstream opening by up to about 2 mm.

3. The insert as claimed in claim 1 wherein said upstream opening is substantially circular and said downstream opening is substantially elliptical, and wherein said filter medium is disposed across said elliptical opening.

4. The insert as claimed in claim 1 wherein said downstream opening is substantially rectangular, and wherein said filter medium is disposed across said rectangular opening.

5. The insert as claimed in claim 1 wherein said hollow passageway comprises one wall that tapers from said larger cross section entry to said smaller cross section exit.

6. The insert as claimed in claim 1 having substantially smooth, gas impervious walls.

7. A cassette, suitable for the sampling of gas containing suspended particulate matter, comprising:

an intake opening comprising at least one internal conduit;

a cassette insert comprising a structure surrounding an internal passageway communicating with said internal conduit; and a filter that cooperates with said internal passageway and is so structured that all gas introduced into said internal passageway passes through said filter;

wherein said internal passageway has a larger cross section upstream end area, a smaller cross section downstream end opening and at least one wall therebetween that is so structured as to cause said particles in said gas to become concentrated as said gas passes from said upstream end area to said downstream end opening;

wherein said intake opening conduit has a smaller cross section than said upstream area of said internal passageway;

wherein said filter and said conduit structures cooperate to cause all the gas that passes through said internal passageway to pass through said filter and to cause at least a substantial quantity of gas borne particles to become entrapped in said filter; and wherein said internal passageway is adapted to communicate with vacuum generating apparatus disposed downstream of said filter and that is adapted to cause ambient gas to be sucked through said intake conduit, said upstream end area, said internal passageway, said downstream opening and said filter medium, and is exhausted to ambient downstream of said filter.

8. The cassette as claimed in claim 7 wherein said filter assembly is in intimate contact with said smaller cross section exit end.

9. The cassette as claimed in claim 8 wherein said internal passageways in said intake cap, said cassette insert and said exit means all have common axes.

10. The cassette as claimed in claim 7 further comprising tubing attached to said intake cap, means to collect ambient gas through said tubing, and vacuum generating means downstream of said filter medium that is adapted to draw ambient gas through said internal passageways and said filter medium.

11. The cassette as claimed in claim 7 wherein said filter assembly is attached to said insert across said exit end opening such that all of said gas that passes through said cassette insert passes through said filter assembly.

12. The cassette as claimed in claim 7 further comprising tubing attached to said intake cap adapted to communicate with said ambient gas.

13. The cassette as claimed in claim 7 further comprising at least one filter that is removable and replaceable.

14. The cassette as claimed in claim 7 wherein said filter is removable without causing a substantial proportion of the particles trapped thereon to be dislodged.

15. The cassette as claimed in claim 7 wherein said particulate matter comprises mold spores.

16. The cassette as claimed in claim 7 wherein said gas comprises air.

17. The cassette as claimed in claim 7 wherein said cassette insert comprises one wall that tapers from said larger cross section entry end to said smaller cross section exit end.

* * * * *